(12) United States Patent
Akiyama et al.

(10) Patent No.: US 10,465,040 B2
(45) Date of Patent: Nov. 5, 2019

(54) PHOTOCURABLE COMPOSITION AND ANTHRACENE DERIVATIVE USED WITH THE SAME

(71) Applicant: NATIONAL INSTITUTE OF ADVANCED INDUSTRIAL SCIENCE AND TECHNOLOGY, Tokyo (JP)

(72) Inventors: Haruhisa Akiyama, Tsukuba (JP); Hideyuki Kihara, Tsukuba (JP); Yoko Okuyama, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 101 days.

(21) Appl. No.: 15/522,186

(22) PCT Filed: Oct. 30, 2015

(86) PCT No.: PCT/JP2015/080656
§ 371 (c)(1),
(2) Date: Apr. 26, 2017

(87) PCT Pub. No.: WO2016/068274
PCT Pub. Date: May 6, 2016

(65) Prior Publication Data
US 2017/0306081 A1    Oct. 26, 2017

(30) Foreign Application Priority Data

Oct. 31, 2014 (JP) ................................ 2014-223289
Aug. 21, 2015 (JP) ................................ 2015-164236

(51) Int. Cl.
| | |
|---|---|
| *C08G 61/10* | (2006.01) |
| *C09J 201/00* | (2006.01) |
| *C09J 199/00* | (2006.01) |
| *C09D 7/40* | (2018.01) |
| *C09D 4/00* | (2006.01) |
| *C09J 11/06* | (2006.01) |
| *C09D 7/63* | (2018.01) |
| *C07C 69/003* | (2006.01) |
| *C07C 69/76* | (2006.01) |
| *C08K 5/12* | (2006.01) |
| *C09D 165/00* | (2006.01) |
| *C09J 165/00* | (2006.01) |

(52) U.S. Cl.
CPC ............ *C08G 61/10* (2013.01); *C07C 69/003* (2013.01); *C07C 69/76* (2013.01); *C08K 5/12* (2013.01); *C09D 4/00* (2013.01); *C09D 7/40* (2018.01); *C09D 7/63* (2018.01); *C09D 165/00* (2013.01); *C09J 11/06* (2013.01); *C09J 165/00* (2013.01); *C09J 201/00* (2013.01); *C07C 2603/24* (2017.05); *C08G 2261/11* (2013.01); *C08G 2261/1426* (2013.01); *C08G 2261/314* (2013.01); *C08G 2261/42* (2013.01)

(58) Field of Classification Search
CPC ...................... C07G 2603/24; C07G 2603/11; C08G 61/10; C08G 2261/11; C08G 2261/42; C08G 2261/1426; C08G 2261/314; C07C 69/76; C07C 69/003; C09J 201/00; C09J 199/00; C08K 5/12; C08D 7/63; C08D 165/00; C08D 7/40; C08D 11/06; C08D 4/00
See application file for complete search history.

(56) References Cited

U.S. PATENT DOCUMENTS

| | | | |
|---|---|---|---|
| 8,933,208 B2 | 1/2015 | Norikane et al. | |
| 9,126,899 B2 | 9/2015 | Norikane | |
| 9,464,216 B2 | 10/2016 | Akiyama et al. | |
| 9,708,493 B2 | 7/2017 | Amara et al. | |
| 2005/0008571 A1 | 1/2005 | Newkome et al. | |
| 2014/0175421 A1 | 6/2014 | Pan et al. | |

FOREIGN PATENT DOCUMENTS

| | | |
|---|---|---|
| EP | 2261738 A2 | 12/2010 |
| JP | 2008-260846 A | 10/2008 |
| JP | 2009-256485 A | 11/2009 |
| JP | 2010-006712 A | 1/2010 |

(Continued)

OTHER PUBLICATIONS

Connal et al.Fabrication of Reversibly Crosslinkable, 3-Dimensionally Conformal Polymeric Microstructures. Advanced Funcitonal Materials. vol. 18. Issue 20. pp. 3315-3322 (2008) (Year: 2008).*
Radl et al. Photo-induced crosslinking and thermal de-crosslinking in polynorbornenes bearing pendant anthracene groups. European Polymer Journal. vol. 52 (2014). pp. 98-104 (Year: 2014).*
PCT/ISA/210, "International Search Report for PCT/JP2015/080656," dated Dec. 8, 2015.
Network Polymer vol. 31, No. 2 (2010), Naoko Yoshie et al., "Reaction Reversibility of Prepolymeers with Anthracene Groups in side Chains and at Chain Ends".
Advanced Functional Materials, 2010, vol. 20, 1561-1567, Hideyuki Kihara et al., Grayscale Photopatterning of an Amorphous Polymer thin Film Prepared by Photopolymerization of a Bisanthracene-Functionalized Liquid-Crystalline Monomer.

(Continued)

*Primary Examiner* — Sanza L. McClendon
(74) *Attorney, Agent, or Firm* — Manabu Kanesaka (57) ABSTRACT

The invention provides a material having a structure including three or more anthracene structures per molecule as a photosensitive unit. That structure allows the material to remain in a liquid state at room temperature due to its reduced crystallinity. After coated on an application member in a liquid state, it is irradiated with light from outside so that it can be cured by way of photocrosslinking, and when heated, it returns back to the original state as the linkage is cleaved. By use of this material it is possible to form a reversibly detachable layer that serves as an adhesive layer at an interface to an application member and a coating layer at the surface of the application member.

8 Claims, 4 Drawing Sheets

(56) References Cited

FOREIGN PATENT DOCUMENTS

| | | |
|---|---|---|
| JP | 2011-256155 A | 12/2011 |
| JP | 2011-256291 A | 12/2011 |
| JP | 2012-045864 A | 3/2012 |
| JP | 2014-037496 A | 2/2014 |
| JP | 2014-098798 A | 5/2014 |
| WO | 2013/081155 A1 | 6/2013 |
| WO | 2013/168712 A1 | 11/2013 |

OTHER PUBLICATIONS

Applied Materials & Interfaces, 2013, vol. 5, 2650-2657, Hideyuki Kihara et al., "Reversible bulk-phase change of anthroyl compounds for photopatterning based on photodimerization in the molten state and thermal back reaction".

Macromolecules, vol. 30, 1997, 2300-2304, George R. Newkome et al., "Detection and Functionalization of Dendrimers Possessing Free Carboxylic Acid Moieties".

ACS Applied Materials & Interfaces, 6, 7933-7941 (2014), Haruhisa Akiyama et al., "Photochemically Reversible Liquefaction and Solidification of Multiazobenzene Sugar-Alcohol Derivatives and Application to Reworkable Adhesives".

Chemistry A European Journal, 19, 17391-17397 (2013), Emi Uchida et al., "Control of the Orientation and Photoinduced Phase Transitions of Macrocyclic Azobenzene".

Advanced Materials, 24, 2353-2356 (2012), Haruhisa Akiyama et al., "Photochemically Reversible Liquefaction and Solidification of Single compounds Based on a Sugar Alcohol Scaffold with multi Azo-Arms".

Chem. Commun., 47, 1770-1772 (2011), Yasuo Norikane et al., "Photoinduced isothermal phase transitions of liquid-crystalline macrocyclic azobenzenes".

Journal of Materials Chemistry, 19, 5956-5694 (2009), Haruhisa Akiyama et al., "Reflection colour changes in cholesteric liquid crystals after the additional and photochemical isomerization of mesogenic azobenzenes tethered to sugar alcohols".

Tetrahedron, 68, 5513-5521 (2012), Hideyuki Kihara et al., "Regioselectivity control of photodimerization of liquid-crystalline cinnamoyl compounds by phase variation: dual functionality of p-terphenyl substituent as a mesogen and a triplet sensitizer".

Advanced Functional Materials, 20, 1561-1567 (2010), Hideyuki Kihara et al., "Grayscale Photopatterning of an Amorphous Polymer Thin Film Prepared by Photopolymerization of a Bisanthracene-Functionalized Liquid-Crystalline Monomer".

Europe Patent Office, "Search Report for European Patent Application No. 15854319.9," dated Mar. 7, 2018.

\* cited by examiner

PHOTOCURABLE COMPOSITION AND ANTHRACENE DERIVATIVE USED WITH THE SAME

RELATED APPLICATIONS

The present application is National Phase of International Application No. PCT/JP2015/080656 filed Oct. 30, 2015, and claims priority from Japanese Applications No. 2014-223289, filed Oct. 31, 2014; and No. 2015-164236, filed Aug. 21, 2015, the disclosure of which is hereby incorporated by reference herein in its entirety.

FIELD OF THE INVENTION

The present invention relates generally to a photo-curable composition, and more specifically to a photo-curable composition capable of fluidization/non-fluidization by irradiation with light and heating, and an anthracene derivative used with such a composition.

BACKGROUND OF THE INVENTION

Among materials whose fluidity varies by light there is a photocurable resin that loses its fluidity when the liquid material is irradiated with light, resulting in solidification, and has found wide use as adhesives, coating agents or the like. Such a photocurable resin cures mainly as polymerization and crosslinking reactions proceed, and the curing reaction is irreversible due to the formation of chemical bonds involved.

Some reversible adhesives include a conventional hot-melt type adhesive, but do not have workability at room temperature because of being liquefied only upon heating. There have also been studies made of adhesives capable of breakdown by thermal decomposition or photo-decomposition after it has cured, but most break down only once.

Apart from this, sugar alcohol derivatives or the like having a polyvalent azobenzene structure have been proposed as an adhesive capable of reversible desorption by light (Patent Publications 1-4, and Non-Patent Publications 1-5). An adhesive comprising this material is capable of repeated adhesion and desorption over and over only by irradiation with light. This repeatability ensues from melting or softening point changes based on the repeatable photoisomerization of azobenzene with the result that a stable state at room temperature can alternate over and over between a liquid phase and a solid phase.

However, the use of an azo dye causes adhesives to be colored in yellow to orange, imposing limitation on the range of use. To obtain a colorless adhesive, it is required to change a photosensitive unit from azobenzene to a transparent one.

Among candidates for the photosensitive unit capable of reversible reactions there is colorless anthracene. It has been known that the anthracene is dimerized by photoreactions, but when heated, the linkage is cleaved off allowing it to return back to the original state. Light-induced phase transition making use of this has already been put forward (Patent Publications 5-10, Non-Patent Publications 6 and 7).

However, this material cannot take on a liquid state at room temperature. A problem with the material used as an adhesive or coating agent is that it must remain in a stable liquid state at room temperature.

PRIOR ARTS

Patent Publications

Patent Publication 1: WO 2013/168712
Patent Publication 2: JP(B) 5561728
Patent Publication 3: WO 2013/081155
Patent Publication 4: JP(A) 2011-256155
Patent Publication 5: JP(A) 2008-260846
Patent Publication 6: JP(B) 5481672
Patent Publication 7: JP(B) 5083980
Patent Publication 8: JP(A) 2012-045864
Patent Publication 9: JP(A) 2014-037496
Patent Publication 10: JP(A) 2014-098798

Non-Patent Publications

Non-Patent Publication 1: ACSAppl. Mater. Interfaces, 6, 7933-7941 (2014)
Non-Patent Publication 2: Chem. Eur. J., 19, 17391-17397 (2013)
Non-Patent Publication 3: Adv. Mater., 24, 2353-2356 (2012)
Non-Patent Publication 4: Chem. Commun., 47, 1770-1772 (2011)
Non-Patent Publication 5: J. Mater. Chem., 19, 5956-5694 (2009)
Non-Patent Publication 6: Tetrahedron, 68, 5513-5521 (2012)
Non-Patent Publication 7: Adv. Funct. Mater., 20, 1561-1567 (2010)

SUMMARY OF THE INVENTION

Objects of the Invention

Having been made with such situations in mind, the present invention has for its object to provide a transparent material that is capable of fluidization (liquid)/non-fluidization (solid) by irradiation with light and heating.

Embodiments of the Invention

To achieve the aforesaid object, the present inventors have made study after study in view of an anthracene derivative that is a colorless, photodimerized, cross-linked group having no absorption in a visible region and capable of bringing about a thermally reversible reaction, and have consequently found a material having a structure including three or more anthracene structure groups per molecule as a photo-sensitive unit, wherein the material remains liquid at room temperature with a decreasing crystallinity; once applied in a liquid state to an application member, the material can be cured via photocrosslinking by irradiation with light; and the material returns back to a liquid state by heating to cleave the linkage. By use of this material, it is possible to obtain a reversibly detachable layer that serves as an adhesive layer at an interface to the application member and a coating layer at the surface of the application member.

The present invention has been accomplished as a result of intensive studies made on the basis of the aforesaid finding, and is embodied as follows.

[1] A photocurable composition composed mainly of an anthracene derivative including three or more anthracene moiety-containing groups per molecule, characterized in that said composition is irradiated with light to make a transition from a fluidization state to a non-fluidization state and even after restored back to room temperature by heating, said composition remains in a fluidization state.

[2] A photocurable composition as recited in [1], characterized in that said anthracene derivative is represented by the following formula 1 or 2:

In formula 1, n is indicative of an integer of 3 to 6, and in formulae 1 and 2, A stands for a group comprising $A_1$ represented by any one of the following formulae a), b) and c) or a group selected from said $A_1$ and the following $A_2$ where said $A_2$ is a group selected from a hydrogen atom, a C1 to C22 alkyl group, and a C2 to C22 alkanoyl group that may be substituted by a chlorine atom, a bromine atom, a fluorine atom or an acetyloxy group, and n A's in formula 1 and all or three or more of four A's in formula 2 are $A_1$.

In formula a), b) or c), X is a group selected from an ester, an ether, a benzyl ether, a ketone, an amine, an amide and a methylene group, Y is a C1 to C20 alkylene group or a C2 to C20 alkylenecarbonyl group, and Z is a group selected from a hydrogen atom, a chlorine atom, a bromine atom, a fluorine atom, a cyano group, a methyl group and a methoxy group.

[3] A photocurable composition as recited in [1] or [2], characterized by further containing a plasticizer.

[4] A photocurable composition as recited in any one of [1] to [3], characterized by being capable of repetition of said non-fluidization/fluidization.

[5] A cured composition, in which a photocurable composition as recited in any one of [1] to [4] is irradiated and cured with light containing ultraviolet light.

[6] A liquefied composition, in which a photocurable composition as recited in any one of [1] to [4] is heated and liquefied.

[7] A coating agent, comprising a photocurable composition as recited in any one of [1] to [4].

[8] An adhesive, comprising a photocurable composition as recited in any one of [1] to [4].

[9] An anthracene derivative, represented by the following formula 1 or 2:

In formula 1, n is indicative of an integer of 3 to 6, and in formulae 1 and 2, A stands for a group comprising $A_1$ represented by any one of the following formulae a), b) and c) or a group selected from said $A_1$ and the following $A_2$ where said $A_2$ is a group selected from a hydrogen atom, a C1 to C22 alkyl group, and a C2 to C22 alkanoyl group that may be substituted by a chlorine atom, a bromine atom, a fluorine atom or an acetyloxy group, and n A's in formula 1 and all or three or more of four A's in formula 2 are $A_1$.

c)

In formula a), b) or c), X is a group selected from an ester, an ether, a benzyl ether, a ketone, an amine, an amide and a methylene group, Y is a C1 to C20 alkylene group or a C2 to C20 alkylene carbonyl group, and Z is a group selected from a hydrogen atom, a chlorine atom, a bromine atom, a fluorine atom, a cyano group, a methyl group and a methoxy group.

Advantages of the Invention

According to the invention described here, it is possible to provide a transparent material which takes on a liquid state having fluidity, but which may make a transition to a solid state upon irradiated with light and again return back to a re-adhesive liquid upon heated.

MODES FOR CARRYING OUT THE INVENTION

The photocurable composition of the invention makes a transition from a fluid state to non-fluidization upon irradiated with light and remains in a fluidization state even after brought back to room temperature by heating once, and is characterized in that an anthracene derivative containing three or more groups, per molecule, that include an anthracene moiety that is a photodimerizable functional group is contained as its main component.

The anthracene derivative of the invention is used for the purpose of linking, per molecule, a plurality of groups containing an anthracene moiety that is a planar molecule having a strong association force so that the degree of freedom can be reduced down enough to lower the crystallinity of the whole molecule and render the solid state instable, resulting in achievement of a fluid state, among which the anthracene derivatives represented by the following formula 1 or 2 are preferable.

(1)

(2)

In formula 1, n is indicative of an integer of 3 to 6, and in formulae 1 and 2, A stands for a group comprising $A_1$ represented by any one of the following formulae a), b) and c) or a group selected from said $A_1$ and the following $A_2$ where said $A_2$ is a group selected from a hydrogen atom, a C1 to C22 alkyl group, and a C2 to C22 alkanoyl group that may be substituted by a chlorine atom, a bromine atom, a fluorine atom or an acetyloxy group, and n A's in formula 1 and all or three or more of four A's in formula 2 are $A_1$.

a)

b)

c)

In formula a), b) or c), X is a group selected from an ester, an ether, a benzyl ether, a ketone, an amine, an amide and a methylene group, Y is a C1 to C20 alkylene group or a C2 to C20 alkylene carbonyl group, and Z is a group selected from a hydrogen atom, a chlorine atom, a bromine atom, a fluorine atom, a cyano group, a methyl group and a hydroxymethyl group.

The anthracene derivative represented by formula 1 is a compound which includes per molecule three or more groups containing an anthracene moiety that is a photodimerizable functional group and in which such plural groups are linked via a spacer comprising a methylene or other like group to a molecule having a plurality of substitutable functional groups (polyfunctional groups) such as a sugar alcohol typically represented by pentaerythritol, xylitol, sorbitol and mannitol.

The aforesaid spacer is necessary for enhancing molecular mobility to stabilize a liquid state, and should have at least one carbon atom.

Such a raw material includes an alkanoic halide, an alkanediol, and an alkane dihalide, each one having reactive functional groups on both its ends; however, it is noted that those having 20 or more carbon atoms are not realistic because price rises and an increased molecular weight causes a lowering of fluidity in a liquid state.

Referring to the manner of bonding the anthracene moiety to the spacer, and taking formula a) as an example, there is the mention of an ether structure, an ester structure, an amide structure or the like represented by the following formula formed by reactions of hydroxyanthracene, anthracenecarboxylic acid, aminoanthracene, chloromethylanthracene or the like represented by the following formula with an alkyl group or the like having an alkyl halide, a hydroxyalkyl, a carboxylic acid site or the like at its end.

The opposite end of the spacer moiety is bonded to the hydroxyl group or the like of the sugar alcohol. By way of example but not by way of limitation, that opposite end may be esterified or etherified with the hydroxyl group of the sugar alcohol, etc.

Of the polyfunctional groups to be substituted, at least three must be substituted by anthracene, but there is no problem arising even when moieties other than the anthracene are introduced into the rest. For instance, there is the mention of just a simple alkyl group free of any anthracene group, an alkyl halide group, and an alkyl group having an acetyl terminal. Such diverse structures will lead to an increase in the number of states, making it difficult to have a crystal structure; understandably, such introduction is rather more effective to stabilize the liquid state (in view of entropy).

For photocuring of the photocurable composition, the photodimerization reaction of anthracene was used. To form a crosslinked product, it is required for that composition to contain a compound having at least a trifunctional anthracene moiety per molecule. The more the anthracene moieties per molecule, the more close-packed the crosslinked structure may become; however, six substituents will suffice to increase the crosslinking density, and more substituents are rather less effective.

After the photoreaction, there is a three-dimensional crosslinked structure formed that loses fluidity and solubility in solvents as well. For this reason, that crosslinked structure is best suited for adhesives, and coating agents.

The light necessary for curing may have a wavelength region of 200 to 400 nm in which the light absorption of anthracene lies. In particular, ultraviolet light in the vicinity of 300 to 400 nm is effective for most of glasses and plastics for the reason that they will have transparency.

The quantity of light for irradiation may be in the range of 3.0 to 80 J/cm$^2$ although varying depending on the thickness of adhesive layers or collating layers.

The photocured composition goes back to a monomer upon heated because the bond that forms the dimer is cleaved out. Significant reverse reaction is all that is needed for liquefication; there is no need for the cured composition to return back to the 100% original structure. Liquefaction becomes possible in association with this reverse reaction.

As a matter of course, too many substituents will render it difficult to thermally liquefy the composition after the reverse reaction. The reverse reaction temperature varies depending on the stereostructure around anthracene. In other words, the temperature needed for liquefication varies depending on a difference in the substitution position of the spacer resulting from a raw material difference as shown just below, and the presence or absence of another substituent. For instance, a compound comprising 9-anthracenecarboxylic acid is subjected to an efficient reverse reaction at nearly 150 to 160° C., resulting in liquefication.

Heating may be carried out by a method for warming the whole composition by thermal conduction, or local heating using electromagnetic waves such as infrared rays, microwaves or white light. For more efficient electromagnetic wave heating, it goes without saying that an electromagnetic wave absorber is preferably mixed in the composition for accelerated heating.

More substituents will result in an increasing molecular size, but it is preferable to make the molecular size relatively small for liquefication. In addition, it is difficult to obtain an inexpensive raw material for 6 or more replaceable polyfunctional groups; in other words, 3 to 6 substituents are effective.

For fluidity control, it is useful to use additives. There is no particular limitation on the additives provided that they should be harmless to photoreactions. For instance, there is the mention of plasticizers such as phthalic acid esters. Addition of liquid additives contributes to an increase in fluidity even with a material having a high viscosity at room temperature.

Some synthesis examples are set out below.

SYNTHESIS EXAMPLE 1

Using a condensing agent (such as N,N-dicyclohexylcarbodiimide: DCC), bromomethylenic acid (such as 11-bromoundecanoic acid) is ester-bonded to a sugar alcohol (such as sorbitol) for the synthesis of a precursor. Then, a plurality of terminal alkyl bromides of the obtained precursor are allowed to react with an anthracene-carboxylic acid (9-anthracenecarboxylic acid) in the presence of diazabicycloundecene (DBU) to obtain an end product via the two-step reaction.

In the aforesaid second synthesis step, anthracene-carboxylic acid is used in 6 or more equivalent weights. Then, if the reaction is stopped en route or the amount of the charging anthracene is reduced down to 6 equivalent weights or less, it is possible to obtain a compound whose terminals have a side chain substituted by anthracene and a side chain composed still of bromide.

SYNTHESIS EXAMPLE 2

That compound may also be synthesized from the side chain side. Tert.-butylbromoundecanoic acid ester is allowed to react with an anthracenecarboxylic acid for the synthesis of an anthracene having a spacer, which is then decomposed by hydrogen chloride to form carboxylic acid terminals. Finally, the anthracene is esterified with sorbitol using a condensing agent to obtain an end product as well.

EXAMPLES

Not by way of limitation, the present invention will now be explained in further details with reference to some examples.

Example 1

Synthesis of 9-anthracene hexamer

Two (2.0) grams of 11-bromoundecanoic acid, 0.176 gram of D-sorbitol and 2.44 grams of tosylic acid DMAP were added to 20 ml of dehydrated dichloromethane, and 1.0 gram of diisopropylcarbodimide was slowly added to the solution under stirring. In a $N_2$ atmosphere, an about 19-hours stirring was carried out at room temperature, the solution was then diluted with dichloromethane for filtration, and the filtrate was concentrated. The concentrate was subjected to column separation using dichloromethane and hexane (3:2) and then further concentrated to obtain 1.29 grams of bromoundecanoic acid hexamer in 80.52% yields.

Zero point five (0.5) gram of bromoundecanoic acid hexamer, 0.48 gram of 9-anthracenecarboxylic acid and 0.33 gram of diazabicycloundecene were added to 20 ml of dehydrated DMF, and the solution was heated and stirred for about 9 hours. The solution was subjected to column separation using chloroform and concentrated to obtain 0.11 gram of a product having 2 or 3 anthracene substituents and 0.61 gram of a product having 4 or 6 anthracene substituents, all the samples being liquid.

It is here to be noted that the products having 2 or 3 and 4 or 5 anthracene substituents were identified from the peak intensity rate of the substituents NMRs.

Figure 1:
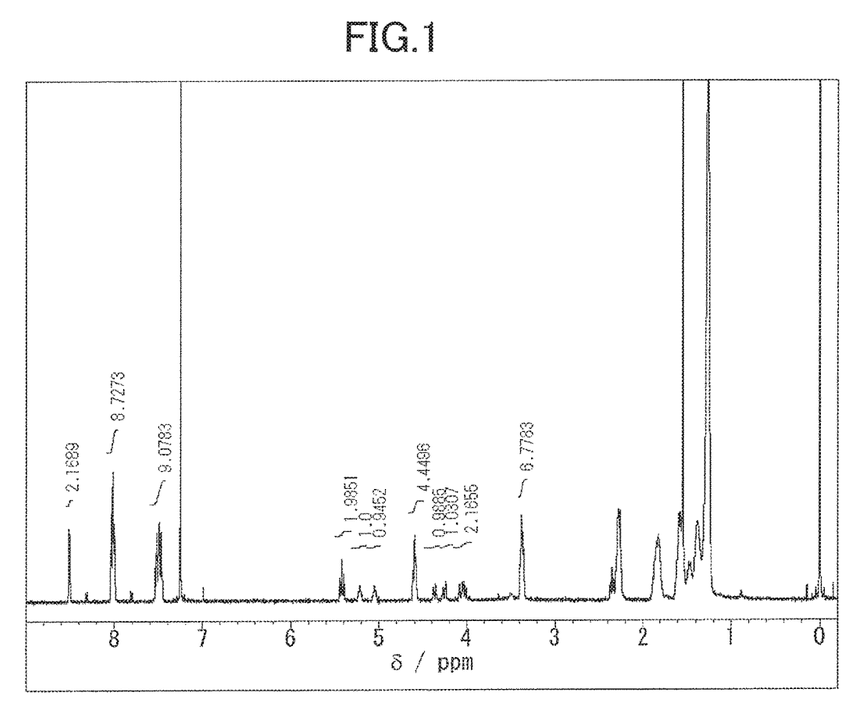
FIG. 1 is indicative of the NMR of a compound having 2 or 3 anthracene substituents.

FIG. 1 is indicative of the NMR of the compounds having 2 or 3 anthracene substituents.

Six peaks corresponding to a total of 8.13H portions appearing at 3.9 to 4.5 ppm and 5.0 to 5.5 ppm are equivalent to the protons (8H/1 molecule) of methylene and methine in the skeleton of the ester-substituted sugar alcohol. On the other hand, three peaks corresponding to a total of 20H portions appearing at 7.5 ppm, 8.0 ppm and 8.5 ppm are derived from protons (9H/1 molecule) bonded to the aromatic ring of anthracene. Hence, the rate of the anthracene introduced is (20/9)/(8/8)=2.2.

Figure 2:
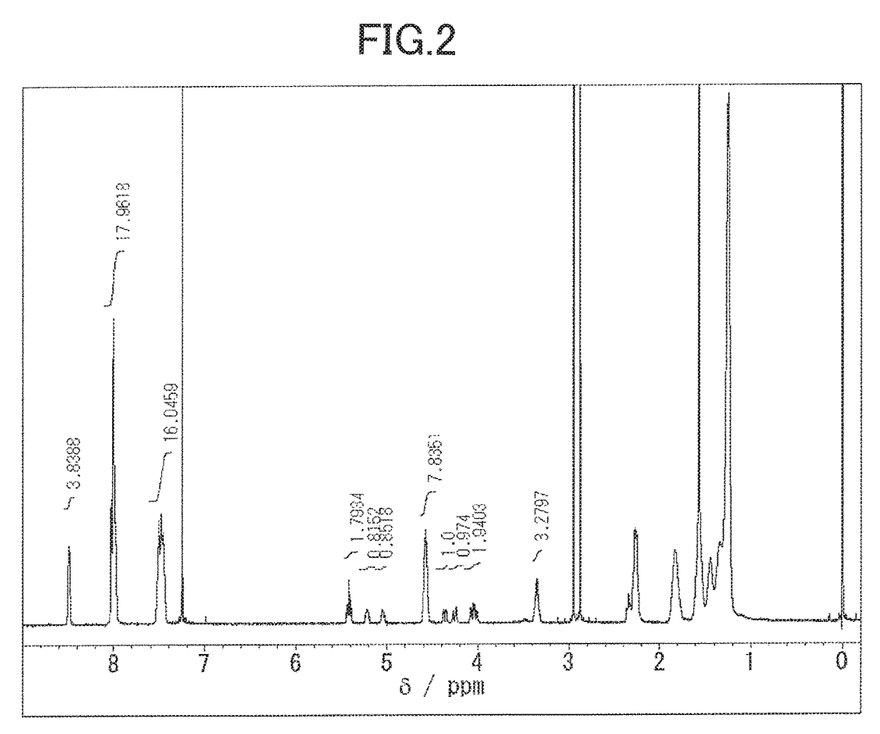
FIG. 2 is indicative of the NMR of a compound having 4 or 5 anthracene substituents.

FIG. 2 is indicative of the NMR of compounds having 4 or 5 anthracene substituents.

Six peaks corresponding to a total of 7.4H portions appearing at 3.9 to 4.5 ppm and 5.0 to 5.5 ppm are equivalent to the protons (8H/1 molecule) of methylene and methine in the skeleton of the ester-substituted sugar alcohol. On the other hand, three peaks corresponding to a total of 48H portions appearing at 7.5 ppm, 8.0 ppm and 8.5 ppm are derived from protons (9H/1 molecule) bonded to the aromatic ring of anthracene. Hence, the rate of the anthracene introduced is (37.85/9)/(7.4/8)=4.5.

Subsequently, these compounds were used as the raw material, and 0.04 gram of 9-anthracenecarboxylic acid and 0.27 gram of diazabicycloundecene were added to 20 ml of dehydrated DMF for an about 6 hours heating and stirring. The product was diluted with dichloromethane and washed with 2M hydrochloric acid, after which it was dried on magnesium sulfate and then concentrated. The concentrate was subjected to column separation using chloroform to obtain 0.16 gram of a liquid anthracene hexamer having a high viscosity in 21.24% yields, with the structure identified by NMR.

Figure 3:
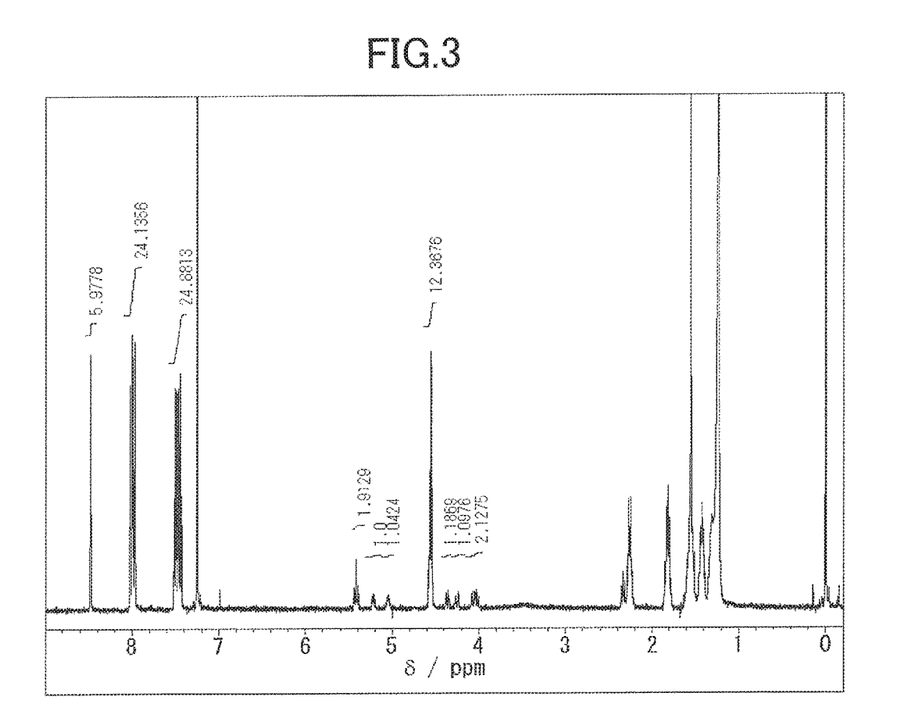
FIG. 3 is indicative of the NMR of a compound having 6 anthracene substituents.

FIG. 3 is indicative of the NMR of a compound having 6 anthracene substituents.

Six peaks corresponding to a total of 8.4H portions appearing at 3.9 to 4.5 ppm and 5.0 to 5.5 ppm are equivalent to the protons (8H/1 molecule) of methylene and methine in the skeleton of the ester-substituted sugar alcohol. On the other hand, three peaks corresponding to a total of 55H portions appearing at 7.5 ppm, 8.0 ppm and 8.5 ppm are derived from protons (9H/1 molecule) bonded to the aromatic ring of anthracene. Hence, the rate of the anthracene introduced is (55/9)/(8.4/8)=5.82.

The synthesized anthracene hexamer was a liquid having a high viscosity. This material was sandwiched between two 10 cm-wide glass substrates over a 1 cm×1 cm area, and the two glass substrates were fixed in place. The two glass substrates were pulled by hands in opposite directions until they ruptured, and the tensile shear bonding strength was measured from the then maximum load. The value was found to be 47.2 N/cm$^2$.

Then, a similarly prepared sample was irradiated with ultraviolet light 365 nm (50 to 100 mW/cm$^2$) for 5 minutes to cure the anthracene hexamer, after which the tensile shear bonding strength was measured. It was found that the adhesive layer did not ruptured right to the end and quartz cracked in 317.4 N/cm$^2$.

Example 2

The hexamer before irradiation with light was found to have a very high viscosity; a plasticizer was here added to it. The mixing ratio between the anthracene hexamer and the plasticizer (dibutylphthalic acid ester) was 1:1 by weight. As a result, there was a highly fluid material obtained, which was used to fix the glass substrates in the same manner to measure the tensile shear bonding strength. Consequently, the glass substrates could be separated off with a force of as little as 0.2 to 0.3 N/cm$^2$.

Then, a similarly prepared sample (having a mixing ratio of 1:1 was irradiated with ultraviolet light 365 nm (50 to 100 mW/cm$^2$) for 5 minutes to cure a 1:1 mixture of anthracene hexamer and plasticizer. By measurement, the tensile shear bonding strength was then found to be 45.5 to 68.2 N/cm$^2$.

As this sample having a mixing ratio of 1:1 was heated at about 170° C. and cooled down, it allowed the adhesive layer to keep on with liquefication even at room temperature. The bonding strength of this liquid to the glasses was 3.1 N/cm$^2$.

The once liquefied sample having a mixing ratio of 1:1 was again exposed to ultraviolet light 365 nm in the two glass substrates for 3 minutes (50 to 100 mW/cm$^2$) with the result that the sample was again cured. By similar measurement, this sample was found to have a tensile shear bonding strength value of as high as 157.2 N/cm$^2$.

Example 3

In this example, the mixing ratio of anthracene hexamer and plasticizer (dibutylphthalic acid ester) was changed to 2:1, and experimentation was carried out under the otherwise same conditions. When 2.8 mg of the mixture sample was sandwiched between two glass substrates over a bonding area of 1 cm$^2$, there could be no measurement carried out because the sample dropped due to the glass's own weight.

Then, a similarly prepared sample having a mixing ratio of 2:1 was irradiated with ultraviolet light 365 nm (50 to 100 mW/cm$^2$) for 5 minutes to cure a 2:1 mixture of anthracene hexamer and plasticizer. The tensile shear bonding strength was then measured to find that there was no peeling taking place even at 176.7 N/cm$^2$.

As this sample having a mixing ratio of 2:1 was heated at about 170° C. for 5 minutes and cooled down, the bonding layer kept a viscous liquid state even at room temperature. The bonding strength of this liquid to the glasses was 6.4 N/cm$^2$.

The once liquefied sample having a mixing ratio of 2:1 was again exposed to ultraviolet light 365 nm in the two glass substrates for 5 minutes (50 to 100 mW/cm$^2$) with the result that the sample was again cured. The tensile shear bonding strength of this sample was measured to find that it was so high that there was no separation taking place even at 196.4 N/cm$^2$.

As this sample having a mixing ratio of 2:1 was heated at about 170° C. for 4 minutes and cooled down, the bonding layer kept a viscous liquid state even at room temperature. The bonding strength of this liquid to the glass was 20.6 N/cm$^2$.

The sample (having a mixing ratio of 2:1) that was again liquefied was again exposed to ultraviolet light 365 nm in the two glass substrates for 5 minutes (50 to 100 mW/cm$^2$) with the result that it was again cured. By similar measurement of tensile shear bonding strength, this sample was found not to separate off even at 201.0 N/cm$^2$.

Then, 1.2 mg of a mixed sample having the same mixing ratio of 2:1 were sandwiched between glass substrates over a bonding area of 1 cm$^2$. The bonding strength was then found to be 0.2 N/cm$^2$.

A similarly prepared sample having a mixing ratio of 2:1, 1.2 mg) was exposed to ultraviolet light 365 nm (50 to 100 mW/cm$^2$) for 5 minutes for curing. By measurement, the sample was found to have a tensile shear bonding strength of 146.1 N/cm$^2$.

Example 4-A

Synthesis of erythritol-skeleton anthracene tetramer

Two point zero (2.0) grams of 11-bromoundecanoic acid, 0.1 gram of pentaerythritol and 2.44 grams of tosylic acid DMAP were added to 20 ml of dehydrated dichloromethane, and 1.0 gram of diisopropylcarbodimide was slowly added to the solution under agitation. In a $N_2$ atmosphere, the solution was stirred at room temperature for about 19 hours, diluted with dichloromethane for filtration, and the filtrate was concentrated. The concentrate was subjected to column separation using dichloromethane and hexane (5:3), and then concentrated to obtain 0.83 gram of a bromoundecanoic acid tetramer in 52.83% yields.

Zero point six five (0.65) gram of the bromoundecanoic acid, 1.0 gram of 9-anthracenecarboxylic acid and 0.62 gram of potassium carbonate were added to 10 ml of dehydrated DMF and stirred at 80° C. for about 18 hours. The solution was subjected to column separation using chloroform and concentrated to obtain 0.97 gram of a liquid anthracene tetramer.

Figure 4:
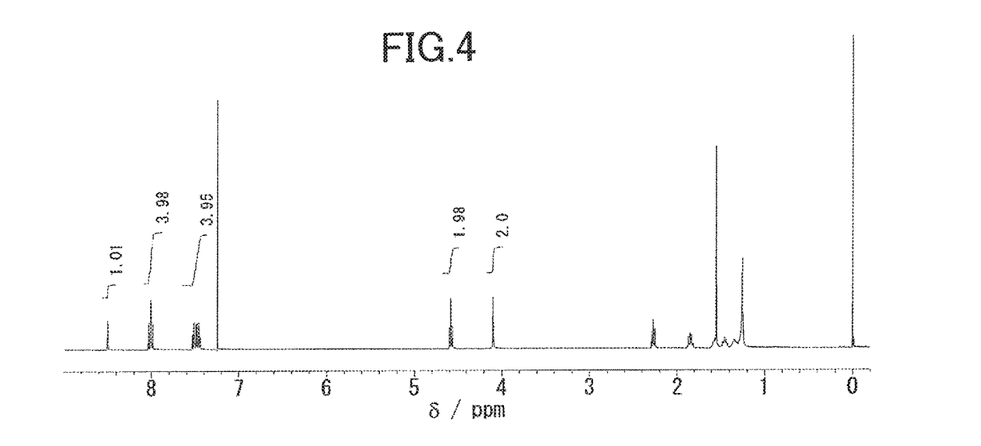
FIG. 4 is indicative of the NMR of a tetramer of anthracene.

FIG. 4 is indicative of the NMR of the anthracene tetramer.

A singlet peak of an 8H portion appearing at 4.10 ppm is equivalent to the protons (8H/1 molecule) of methylene in the erythritol skeleton substituted by ester. On the other hand, a peak of an 8H portion at 4.58 ppm is derived from the methylene bonded to the anthracene-carbonyloxy group and three peaks appearing at 7.5 ppm, 8.0 ppm and 8.5 ppm are done from the proton (36H/1 molecule) bonded to the aromatic ring of anthracene. In other words, 4 units of anthracene are introduced.

Example 4-B

Bonding Testing of Erythritol-Skeleton Anthracene Tetramer

The synthesized anthracene tetramer was a highly viscous liquid. This material was sandwiched between two 1.5 cm-wide glass substrates over a 1.5 cm×0.5 cm area to prepare a sample that was then irradiated with ultraviolet light 365 nm (50 to 100 mW/cm$^2$) for 10 minutes to cure the anthracene tetramer. The two glass substrates were pulled by hands in the opposite directions and the maximum load then applied on them was taken as the tensile shear bonding strength. The value was 231.0 N/cm$^2$.

The sample that prepared in the same way as mentioned above was heated at 180° C. for 11 minutes and then cooled down to room temperature. As a result of pulling the sample, it slipped under a load of 6.0 N/cm$^2$ without separation. From this, the sample was found to be liquefied.

Where the aforesaid sample was allowed to slip 1 mm, it was again irradiated with ultraviolet light 365 nm (50 to 100 mW/cm$^2$) for 10 minutes to cure the anthracene tetramer. The tensile shear bonding strength was then measured with the result that the adhesive layer did not rupture right to the end and the quartz cracked at 702.0 N/cm$^2$.

Example 5-A

Synthesis of 1-anthracene hexamer

Zero point six five (0.65) gram of bromoundecanoic acid, 1.0 gram of 1-anthracenecarboxylic acid and 0.62 gram of potassium carbonate were added to 10 ml of dehydrated DMF, and the solution was stirred at 80° C. for about 6 hours. The solution was subjected to column separation using chloroform and then concentrated to obtain 0.95 gram of a liquid sample.

Figure 5:
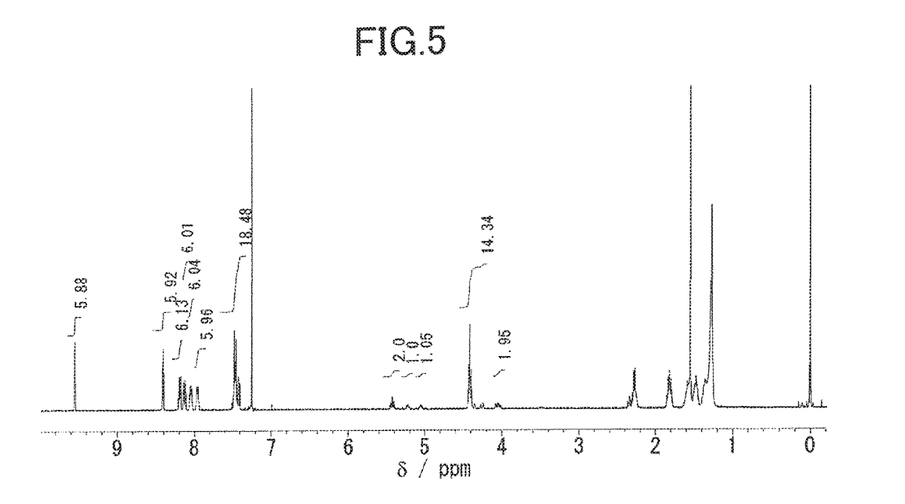
FIG. 5 is indicative of the NMR of a hexamer of 1-anthracene.

FIG. 5 is indicative of the NMR of substituted 1-anthracene.

Four peaks appearing at 4.0-4.1 ppm (2H), 4.3 ppm (1H), 5.1 ppm (1H), 5.2 ppm (1H) and 5.4 ppm (2H) and a 2H portion of 14H at 4.4 ppm are equivalent to the protons of methylene and methine (8H/1 molecule) in the ester-substituted sugar alcohol skeleton (8H/1 molecule). On the other hand, seven peaks corresponding to a total of 54H portions appearing at 7.4-7.5 ppm (18H), 7.9 ppm (6H), 8.0 ppm (6H), 8.1 ppm (6H), 8.2 ppm (6H), 8.4 ppm (6H) and 9.5 ppm (65H) are derived from the protons (9H/1 molecule) bonded to the aromatic ring of anthracene. From the integral ratio, the product here is found to be a hexa-substituted anthracene.

Example 5-B

Fluidization/Non-Fluidization Testing of 1-anthracene Hexamer

The 1-anthracene hexamer was a highly viscous liquid. For this reason, it was mixed with dibutylphthalic acid ester at a ratio of 2:1, and the mixture was sandwiched between two 1-cm wide glass substrates over a 1 cm×1 cm area to fix them in place. It was irradiated with ultraviolet light with the result that it was cured and remained immobilized. Once it was heated at 200° C. for 5 minutes, it became soft enough to cause movement of the slide glass even upon cooled down to room temperature. Once more irradiation with ultraviolet caused it to be again cured and remain immobilized.

Example 6-A

Synthesis of 2-anthracene hexamer

Zero point five six (0.56) gram of a bromoundecanoic acid hexamer, 1.2 grams of 2-anthracenecarboxylic acid and 0.70 gram of potassium carbonate were added to 20 ml of dehydrated DMF, and the solution was stirred at 80° C. for about 6 hours. The solution was subjected to column separation using chloroform and concentrated to obtain 0.46 gram. This sample was solid.

Figure 6:
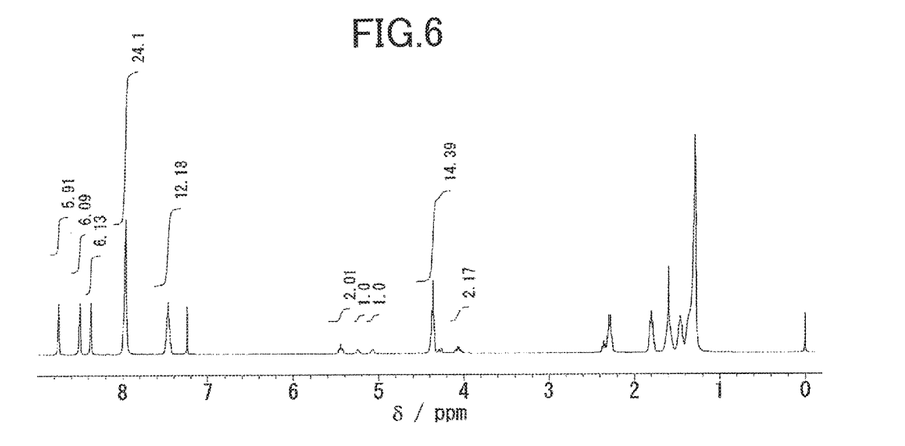
FIG. 6 is indicative of the NMR of a hexamer of 2-anthracene.

FIG. 6 is indicative of the NMF of the substituted 2-anthracene.

Four peaks appearing at 4.0-4.1 ppm, 5.1 ppm, 5.2 ppm and 5.4 ppm and a 2H portion of 14H at 4.4 ppm are equivalent to the protons (8H/1 molecule) of methylene and methine in the ester-substituted sugar alcohol skeleton. On the other hand, five peaks corresponding to a total of 54H portions appearing at 7.5 ppm, 8.0 ppm, 8.4 ppm, 8.5 ppm and 8.7 ppm are derived from the protons (9H/1) bonded to the aromatic ring of anthracene.

Example 6-B

Bonding Testing of 2-anthracene Hexamer

Ten (10) mg of a 1:1 liquid mixture of 2-anthracene and dibromo-hexane were sandwiched between 2.7-cm wide slide glasses over a superposed width of about 1.5 cm and irradiated with ultraviolet light for 2 minutes with the result that it was cured and remained immobilized. Once it was heated at 190° C. for 2 minutes, it separated off.

What is claimed is:

1. A photocurable composition composed mainly of a liquid anthracene derivative including three or more anthracene moiety-containing groups per molecule,
    wherein said anthracene derivative is represented by the following formula 1 or 2:

(1)

(2)

where in formula 1, n is indicative of an integer of 3 to 6, and in formulae 1 and 2, A stands for a group comprising $A_1$ represented by any one of the following formulae a), b) and c) or a group selected from said $A_1$ and the following $A_2$ where said $A_2$ is a group selected from a hydrogen atom, a C1 to C22 alkyl group, and a C2 to C22 alkanoyl group that may be substituted by a chlorine atom, a bromine atom, a fluorine atom or an acetyloxy group, and n A's in formula 1 and all or three or more of four A's in formula 2 are $A_1$;

a)

b)

c)

where in formula a), b) or c), X is a group selected from an ester, an ether, a benzyl ether, a ketone, an amine, an amide and a methylene group, Y is a C1 to C20 alkylene group or a C2 to C20 alkylenecarbonyl group, and Z is a group selected from a hydrogen atom, a chlorine atom, a bromine atom, a fluorine atom, a cyano group, a methyl group and a methoxy group, and wherein said composition is irradiated with light to make a transition from a fluidization state to a non-fluidization state and even after restored back to room temperature by heating, said composition remains in a fluidization state.

2. A photocurable composition composed mainly of a liquid anthracene derivative including three or more anthracene moiety-containing groups per molecule, and a plasticizer;
wherein said composition is irradiated with light to make a transition from a fluidization state to a non-fluidization state and even after restored back to room temperature by heating, said composition remains in a fluidization state.

3. A photocurable composition as recited in claim 1, wherein the composition is capable of repetition of said non-fluidization/fluidization.

4. A cured composition, in which a photocurable composition as recited in claim 1 is irradiated with light containing ultraviolet light for curing.

5. A liquefied composition, in which a photo-curable composition as recited in claim 1 is heated and liquefied.

6. A coating agent, comprising a photocurable composition as recited in claim 1.

7. An adhesive, comprising a photocurable composition composed mainly of a liquid anthracene derivative including three or more anthracene moiety-containing groups per molecule,
wherein said composition is irradiated with light to make a transition from a fluidization state to a non-fluidization state and even after restored back to room temperature by heating, said composition remains in a fluidization state.

8. An anthracene derivative, represented by the following formula 1 or 2:

(1)

(2)

where in formula 1, n is indicative of an integer of 3 to 6, and in formulae 1 and 2, A stands for a group comprising $A_1$ represented by any one of the following formulae a), b) and c) or a group selected from said $A_1$ and the following $A_2$ where said $A_2$ is a group selected from a hydrogen atom, a C1 to C22 alkyl group, and a C2 to C22 alkanoyl group that may be substituted by a chlorine atom, a bromine atom, a fluorine atom or an acetyloxy group, and n A's in formula 1 and all or three or more of four A's in formula 2 are $A_1$;

a)

b)

c)

where in formula a), b) or c), X is a group selected from an ester, an ether, a benzyl ether, a ketone, an amine, an amide and a methylene group, Y is a C1 to C20 alkylene group or a C2 to C20 alkylene carbonyl group, and Z is a group selected from a hydrogen atom, a chlorine atom, a bromine atom, a fluorine atom, a cyano group, a methyl group and a methoxy group.

* * * * *